(12) United States Patent
Sears et al.

(10) Patent No.: US 7,806,933 B2
(45) Date of Patent: Oct. 5, 2010

(54) SYSTEM AND METHOD FOR STABILIZING A PROSTHETIC DEVICE

(75) Inventors: William Sears, St. Leonards (AU);
Randall Allard, Germantown, TN (US);
Hai Trieu, Cordova, TN (US); Frank Bono, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 668 days.

(21) Appl. No.: 10/800,909

(22) Filed: Mar. 15, 2004

(65) Prior Publication Data

US 2005/0203626 A1    Sep. 15, 2005

(51) Int. Cl.
*A61F 2/44* (2006.01)
(52) U.S. Cl. ................................... 623/17.11
(58) Field of Classification Search .... 623/17.11–17.16
See application file for complete search history.

(56) References Cited

U.S. PATENT DOCUMENTS

| | | | | |
|---|---|---|---|---|
| 4,454,612 A * | 6/1984 | McDaniel et al. | ........ | 623/23.37 |
| 4,759,769 A * | 7/1988 | Hedman et al. | .......... | 623/17.13 |
| 4,772,287 A * | 9/1988 | Ray et al. | ................ | 623/17.12 |
| 5,401,269 A * | 3/1995 | Buttner-Janz et al. | .... | 623/17.15 |
| 5,458,642 A | 10/1995 | Beer et al. | | |
| 5,702,454 A | 12/1997 | Baumgartner | | |
| 5,755,797 A | 5/1998 | Baumgartner | | |
| 5,776,197 A * | 7/1998 | Rabbe et al. | ............. | 623/17.15 |
| 5,782,832 A * | 7/1998 | Larsen et al. | .................. | 606/61 |
| 5,827,328 A | 10/1998 | Buttermann | | |
| 5,888,226 A * | 3/1999 | Rogozinski | .............. | 623/17.16 |
| 5,895,428 A * | 4/1999 | Berry | ...................... | 623/17.15 |
| 6,063,121 A * | 5/2000 | Xavier et al. | ............. | 623/17.15 |
| 6,156,067 A * | 12/2000 | Bryan et al. | ............. | 623/17.15 |
| 6,350,283 B1 * | 2/2002 | Michelson | ............... | 623/17.11 |
| 6,387,130 B1 * | 5/2002 | Stone et al. | .............. | 623/17.16 |
| 6,419,706 B1 * | 7/2002 | Graf | ........................ | 623/17.16 |
| 6,520,996 B1 * | 2/2003 | Manasas et al. | ............ | 623/23.5 |
| 6,527,804 B1 * | 3/2003 | Gauchet et al. | .......... | 623/17.12 |
| 6,576,016 B1 * | 6/2003 | Hochshuler et al. | ...... | 623/17.15 |
| 6,579,320 B1 * | 6/2003 | Gauchet et al. | .......... | 623/17.15 |
| 6,579,321 B1 * | 6/2003 | Gordon et al. | ........... | 623/17.16 |
| 6,582,466 B1 * | 6/2003 | Gauchet | .................. | 623/17.11 |

(Continued)

FOREIGN PATENT DOCUMENTS

WO    WO 03/094806    11/2003

(Continued)

OTHER PUBLICATIONS

Patent Cooperation Treaty—European Patent Office, "Notification of Transmittal of the International Search Report and the Written Opinion of the International Searching Authority, or the Declaration," International Application No. PCT/US2005/008722, Mar. 15, 2005, 6 pages.

*Primary Examiner*—David J Isabella
*Assistant Examiner*—Ann Schillinger

(57) ABSTRACT

A motion-preserving implant device for insertion between two bones is disclosed. The motion-preserving implant includes a first plate for engaging with a first bone and a second plate for engaging with a second bone. An articulation member is positioned between the two plates and a motion-controlling member attached to one or both of the plates. In some embodiments, the motion-controlling member is configured to constrain, dampen, and/or bumper the relative motion between the two plates.

26 Claims, 9 Drawing Sheets

U.S. PATENT DOCUMENTS

| | | | |
|---|---|---|---|
| 6,733,532 B1 * | 5/2004 | Gauchet et al. | 623/17.12 |
| 2002/0128715 A1 * | 9/2002 | Bryan et al. | 623/17.15 |
| 2002/0151978 A1 * | 10/2002 | Zacouto et al. | 623/17.12 |
| 2002/0156528 A1 * | 10/2002 | Gau | 623/17.11 |
| 2003/0045939 A1 * | 3/2003 | Casutt | 623/17.15 |
| 2003/0045940 A1 * | 3/2003 | Eberlein et al. | 623/17.16 |
| 2003/0135277 A1 * | 7/2003 | Bryan et al. | 623/17.12 |
| 2003/0233146 A1 * | 12/2003 | Grinberg et al. | 623/17.14 |
| 2003/0236571 A1 * | 12/2003 | Ralph et al. | 623/17.13 |
| 2004/0030387 A1 * | 2/2004 | Landry et al. | 623/16.11 |
| 2004/0082999 A1 * | 4/2004 | Mathys et al. | 623/17.11 |
| 2004/0093082 A1 * | 5/2004 | Ferree | 623/17.11 |
| 2004/0153160 A1 * | 8/2004 | Carrasco | 623/17.15 |
| 2004/0193273 A1 * | 9/2004 | Huang | 623/17.12 |

FOREIGN PATENT DOCUMENTS

| | | |
|---|---|---|
| WO | WO 2004/016217 A2 | 2/2004 |
| WO | WO 2004/016217 A3 | 2/2004 |

* cited by examiner

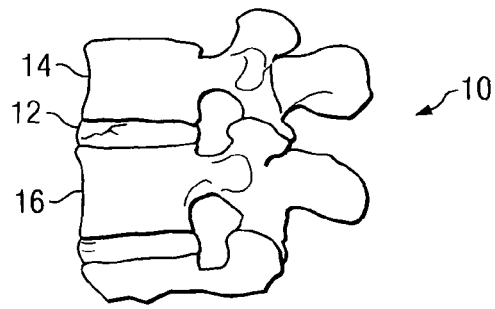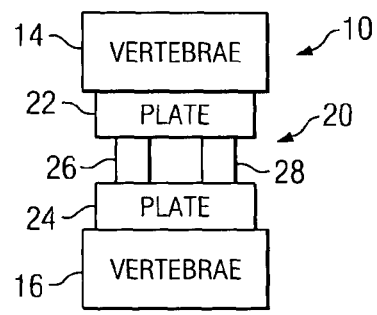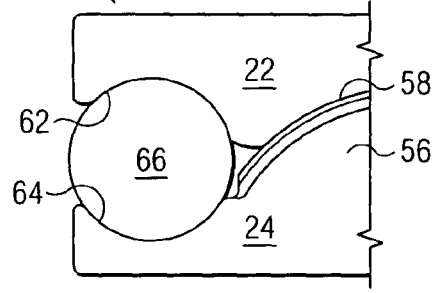

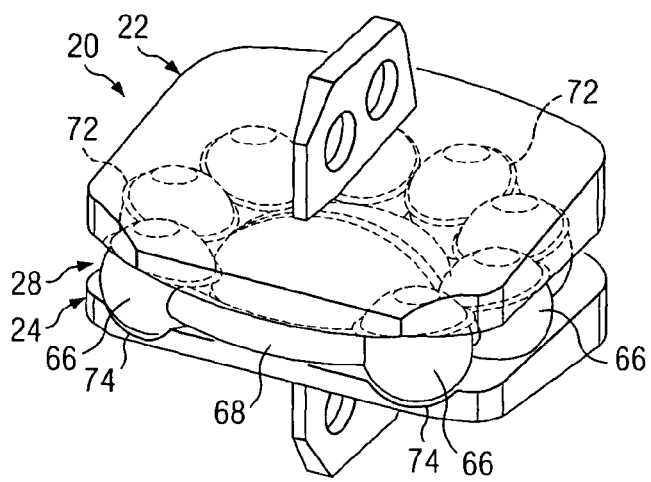
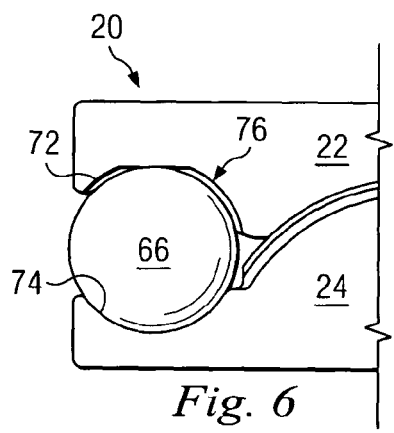
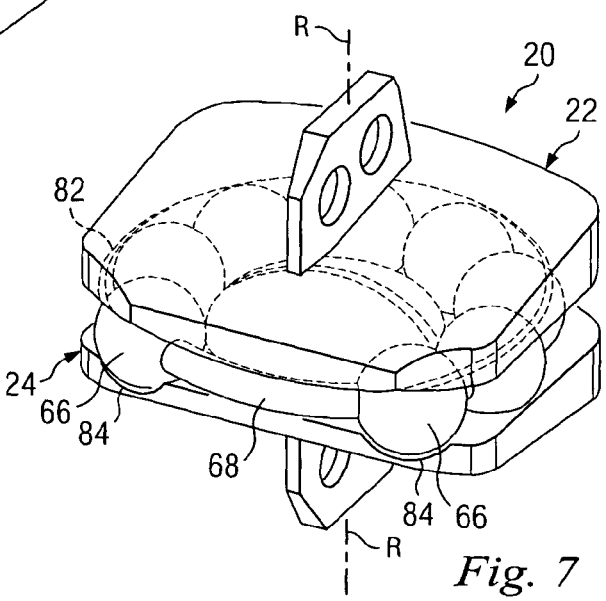
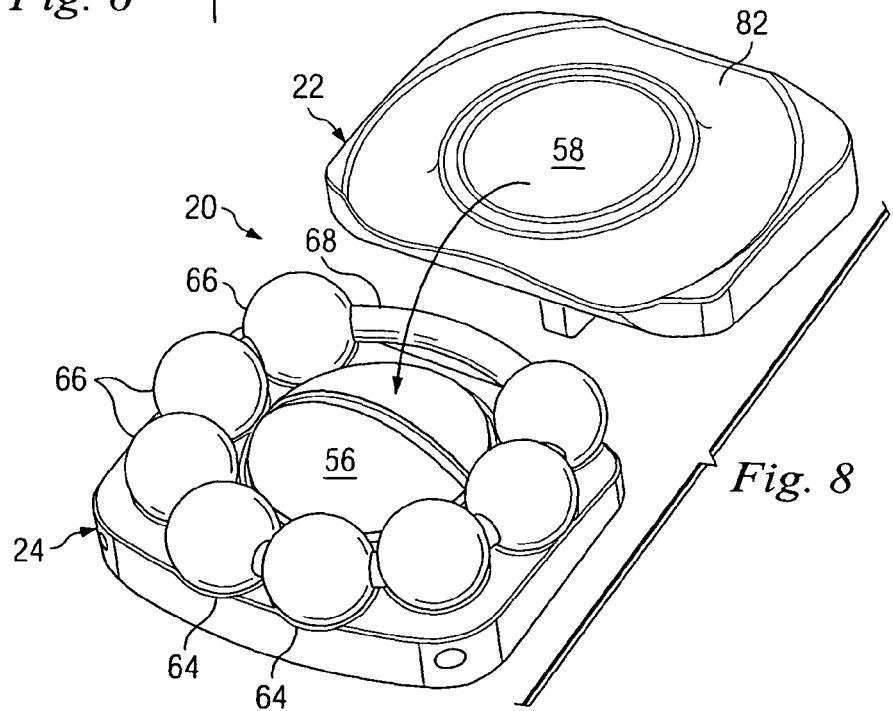

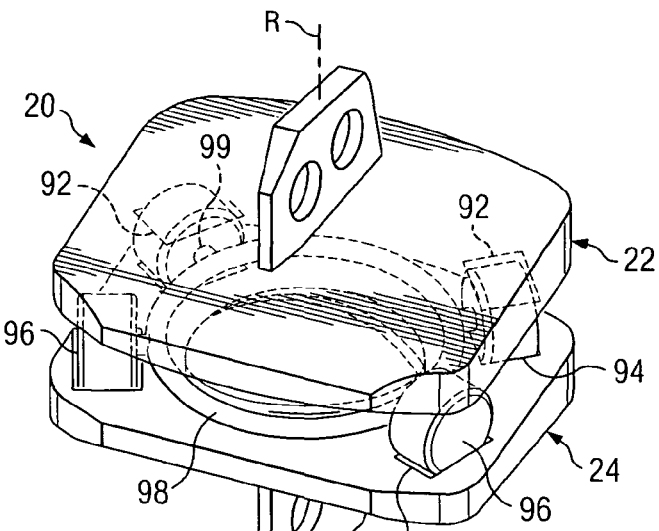
Fig. 9
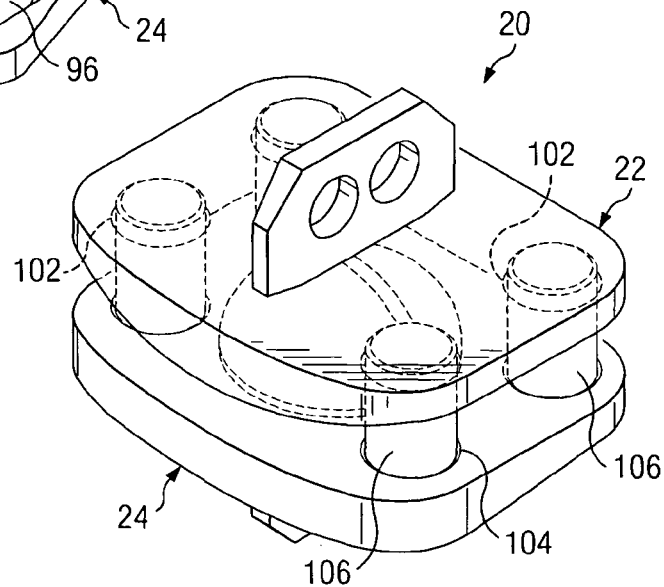
Fig. 11
Fig. 10
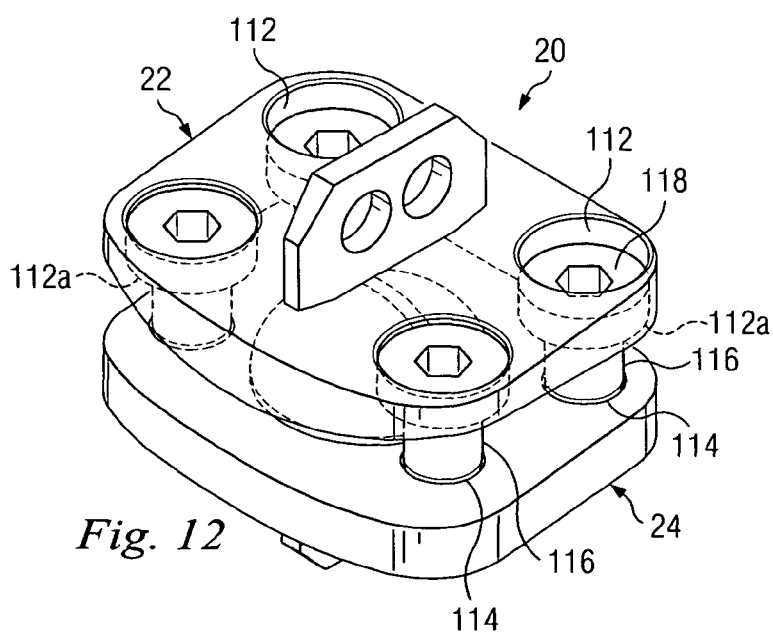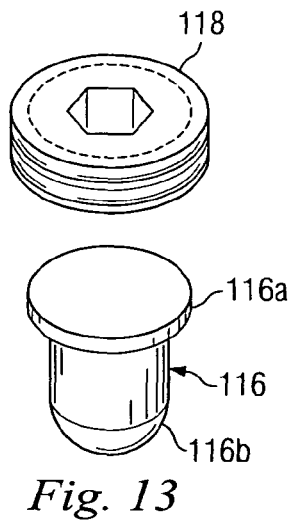
Fig. 12
Fig. 13

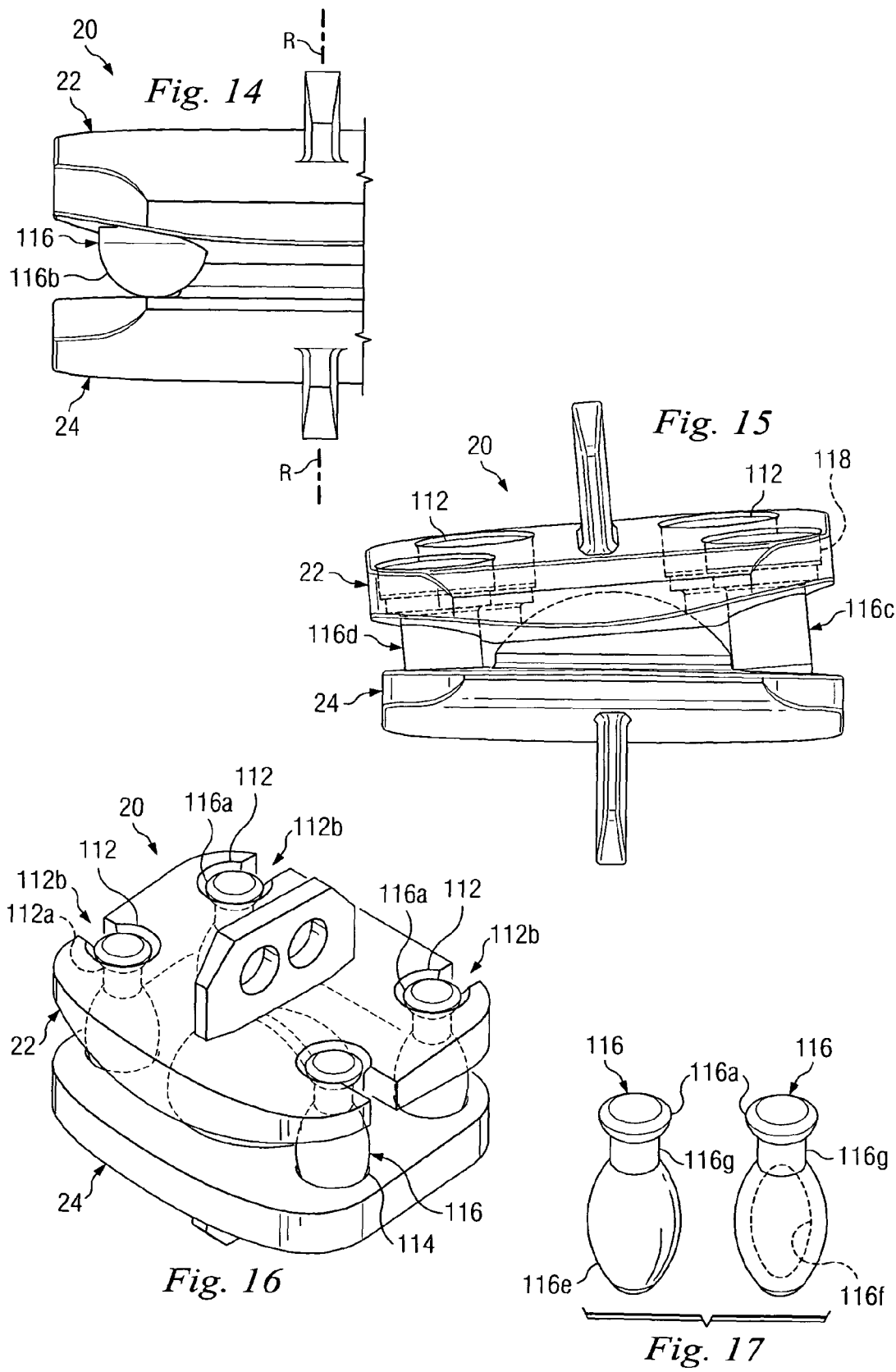

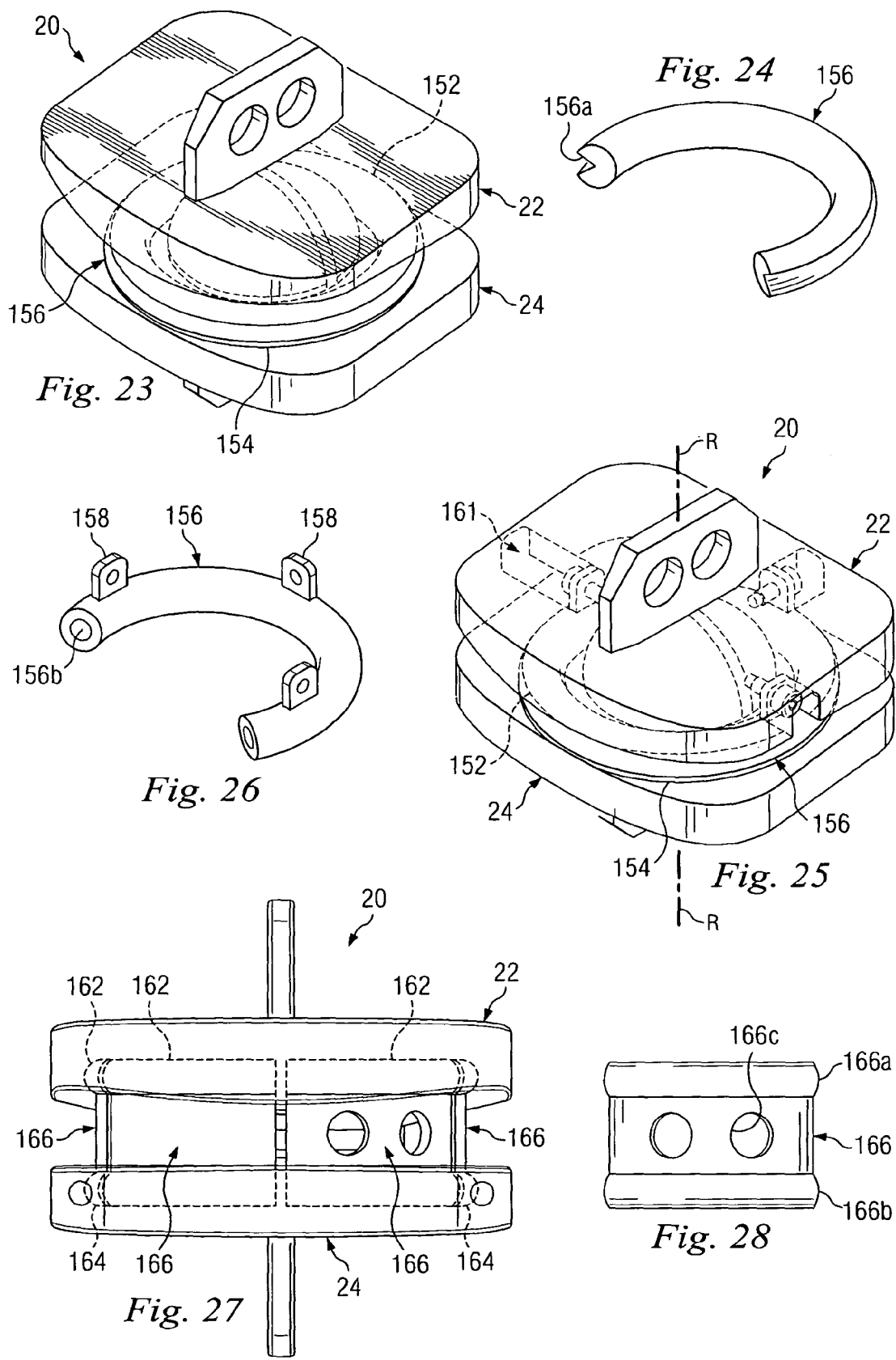

SYSTEM AND METHOD FOR STABILIZING A PROSTHETIC DEVICE

FIELD

The present disclosure relates generally to the field of orthopedics, and joint implants used therein. In some embodiments, the present disclosure relates to intervertebral prosthetic joints for use in the total or partial replacement of a natural intervertebral disc, and methods for use therewith.

BACKGROUND

In the treatment of diseases, injuries or malformations to bone joints, such as those affecting spinal motion segments, and especially those affecting disc tissue, it has long been known to remove some or all of a degenerated, ruptured or otherwise failing disc. In cases involving intervertebral disc tissue that has been removed or is otherwise absent from a spinal motion segment, corrective measures are taken to ensure the proper spacing of the vertebrae formerly separated by the removed disc tissue.

In some instances, the two adjacent vertebrae are fused together using transplanted bone tissue, an artificial fusion component, or other compositions or devices. Spinal fusion procedures, however, have raised concerns in the medical community that the bio-mechanical rigidity of intervertebral fusion may predispose neighboring spinal motion segments to rapid deterioration. More specifically, unlike a natural intervertebral disc, spinal fusion prevents the fused vertebrae from pivoting and rotating with respect to one another. Such lack of mobility tends to increase stresses on adjacent spinal motion segments.

In other instances, intervertebral disc arthroplasty devices have been proposed for preventing the collapse of the intervertebral space between adjacent vertebrae while maintaining a certain range of pivotal and/or rotational motion therebetween. Such devices typically include articular elements positioned between upper and lower plates, which are further attached to respective superior and inferior vertebrae. The articular elements are typically configured to allow the vertebrae to pivot and/or rotate relative to one another. These motion-preserving devices, however, can result in damage from un-constrained movement. Such movement, or lack of stabilization, can exacerbate disc replacement recovery for patients who have spinal deformities such as scoliosis or spondylolisthesis.

In one embodiment, a motion-preserving implant device for insertion between two bones, such as but not limited to vertebrae, is provided. The motion-preserving implant includes a first plate for engaging with a first bone and a second plate for engaging with a second bone. An articulation member is positioned between the two plates and a motion-controlling member attached to one or both of the plates or is positioned between both plates. In some embodiments, the motion-controlling member is configured to constrain, dampen, and/or bumper the relative motion between the two plates.

In another embodiment, a spinal implant for insertion between two vertebral bodies is provided. The spinal implant includes a first plate for engaging with the first vertebral body and a second plate for engaging with the second vertebral body. The spinal implant also includes an articulation member positioned between the two plates and an elastic motion-controlling member attached to one or both of the plates or positioned between the plates. In some embodiments, the articulation member and the motion-controlling member are configured to provide pivotal and rotational movement between the two vertebral bodies. Also in some embodiments, the articulation member is configured to provide rotational and translational movement between the two vertebral bodies.

A method for inserting a motion-preserving implant between two bones is also provided. In one embodiment, the method includes determining a desired shape of the motion-preserving implant and determining a degree of movement for the motion-preserving implant. One or more elastic members are selected according to the determinations of shape and degree of movement, and the one or more elastic members are assembled into the motion-preserving implant. Once assembled, the motion-preserving implant device is inserted between the two bones.

A kit for use in a surgery addressing a joint between two bones is also provided. In one embodiment, the kit includes at least one motion-preserving implant, the motion-preserving implant having at least one recess for receiving at least one elastic member. The kit also includes a plurality of elastic members for use with the motion-preserving implant. The plurality of elastic members are capable of providing a plurality of different configurations of a motion-preserving implant when received therein.

BRIEF DESCRIPTION OF THE DRAWINGS

FIG. 1 is a lateral view of a portion of a vertebral column as an example in which one or more embodiments of the present invention can be implemented.

FIG. 2 is a block diagram of a motion-preserving implant device according to some embodiments of the present invention.

FIGS. 3a, 3b, and 4-39 are various perspective, cross sectional, and exploded views of many different motion-preserving implants according to various embodiments of the present invention.

DESCRIPTION

Figure 18:
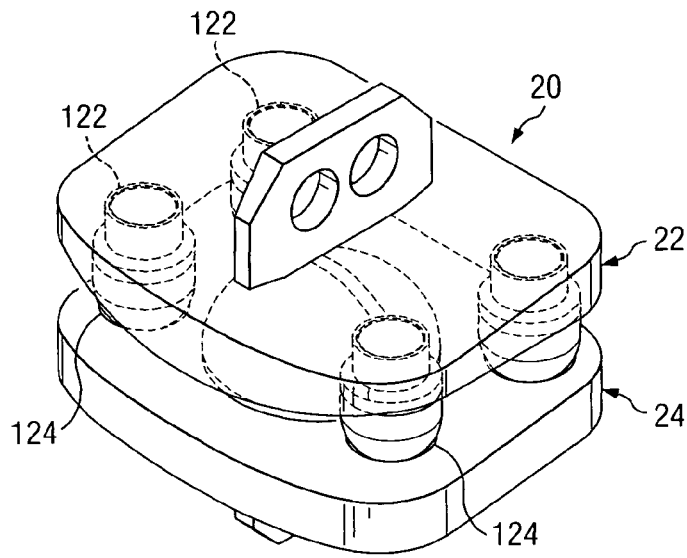

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. As such, individual features of separately described embodiments can be combined to form additional embodiments. In addition, reference numerals are repeated throughout many of the embodiments. Such repetition does not indicate that features of some embodiments must be or should be used with other embodiments. Instead, a wide assortment of different embodiments with one or more features from various drawings and discussions is intended.

Referring to FIG. 1, the numeral 10 refers to a human anatomy having a joint location in which one or more embodiments of the present invention can be implemented. In this example, the human anatomy includes a spine with an injured, diseased, or otherwise damaged intervertebral disc 12 extending between vertebrae 14, 16. Some or all of the damaged disc 12 may be replaced by an intervertebral disc prosthesis according to one or more embodiments of the present invention. Although spinal products are discussed in detail, other embodiments are anticipated, including those related to large-scale orthopedics such as hips and knees, small scale orthopedics such as fingers and wrists, and dental-related products.

Referring to FIG. 2, continuing with the present example of a spinal implant, a motion-preserving implant device 20 can be placed between the two spinal members (vertebrae 14 and 16 in the present embodiment). The device 20 includes a first plate 22 for engaging with the first (e.g., superior) vertebrae 14 and a second plate 24 for engaging with the second (e.g., inferior) vertebrae 16. The device 20 further includes an articulation member 26 positioned between the two plates 22, 24. In some embodiments, the articulation member 26 can be a separate structure from either or both of the plates 22, 24, such as is disclosed in U.S. Pat. Nos. 5,674,296, 6,019,792, and U.S. Published Application Nos. 2002/0035400 and 2003/0199982, which are hereby incorporated by reference. In other embodiments, the articulation member 26 can be integral with or otherwise connected to one or both of the plates 22, 24, such as is disclosed in U.S. Pat. Nos. 5,258,031, 6,113,637, and U.S. Published Application No. 2003/0208273, which are hereby incorporated by reference. For the sake of example, continued reference to the plates 22, 24 and the articulation member 26 will be made to the embodiment disclosed in U.S. Published Application No. 2003/0208273.

In addition to the articulation member 26, a motion-controlling member 28 is interposed between the two plates 22, 24. The motion-controlling member 28 can be attached to one or both of the plates 22, 24, and can include one or more components disposed in various locations. Also, the one or more components can provide various functions, including constraining, cushioning, or dampening the relative motion between the two plates 22, 24.

Referring to FIGS. 3a-8, in some embodiments, the prosthetic device 20 provides relative pivotal and rotational movement between the adjacent vertebral bodies to maintain or restore motion substantially similar to the normal bio-mechanical motion provided by a natural intervertebral disc. More specifically, the plates 22, 24 are permitted to pivot relative to one another about a number of axes, including lateral or side-to-side pivotal movement about longitudinal axis L and anterior-posterior pivotal movement about a transverse axis T. It should be understood that in some embodiments of the disclosure, the plates 22, 24 are permitted to pivot relative to one another about any axes that lies in a plane that intersects longitudinal axis and transverse axis.

Furthermore, in some embodiments, the plates 22, 24 are permitted to rotate relative to one another about a rotational axis R. Although the prosthetic device 20 has been illustrated and described as providing a specific combination of articulating motion, it should be understood that other combinations of articulating movement are also possible, such as, for example, relative translational or linear motion along the plane defined by the axes L and T, and such movement is contemplated as falling within the scope of the present disclosure.

Although the plates 22, 24 of prosthetic device 20 may be formed from a wide variety of materials, in some embodiments of the disclosure, the plates 22, 24 are formed of a cobalt-chrome-molybdenum metallic alloy (ASTM F-799 or F-75). Also in the present embodiment, at least a portion of the plates can be coated with an amorphous oxide coating. However, in alternative embodiments of the disclosure, the plates 22, 24 may be formed of other materials such as titanium, stainless steel, ceramic, polymeric material such as polyethylene, or any other biocompatible material that would be apparent to one of ordinary skill in the art.

The plates 22, 24 each include a bearing surface 30, 32, respectively, that may be positioned in direct contact with vertebral bone and may be coated with a bone-growth promoting substance, for example a hydroxyapatite coating formed of calcium phosphate. Additionally, the bearing surfaces 30, 32 of the plates 22, 24, respectively, may be roughened prior to being coated with the bone-growth promoting substance to further enhance bone on-growth. Such surface roughening may be accomplished by way of, for example, acid etching, knurling, application of a bead coating, or other methods of roughening that would occur to one of ordinary skill in the art.

In some embodiments, the articulation member 26 includes a projection 56 having a convex shape, which may be configured as a spherical-shaped ball (half of which is shown). It should be understood that other configurations of the projection 56 are also contemplated, such as, for example, cylindrical, elliptical or other arcuate configurations or possibly non-arcuate configurations. It should also be understood that the remaining portion of plate 22 may take on planar or non-planar configurations, such as, for example, an angular or conical configuration extending about the projection 56.

Continuing with the present example, the plate 22 includes a recess 58. In some embodiments, the recess 58 has a concave shape, and is configured as a spherical-shaped socket. However, it should be understood that other configurations of the recess 58 are also contemplated, such as, for example, cylindrical, elliptical or other arcuate configurations or possibly non-arcuate configurations.

Although the concave recess 58 is illustrated as having a generally smooth, uninterrupted articular surface, it should be understood that a surface depression or cavity may be defined along a portion of the recess 58 to provide a means for clearing out matter, such as particulate debris, that is disposed between the abutting plates 22, 24. In such case, the convex articular surface of the projection 56 may alternatively define a generally smooth, uninterrupted articular surface. In other embodiments, each of the convex projection 56 and the concave recess 58 may define a surface depression to facilitate removal of particulate matter disposed between the abutting plates 22, 24. In still other embodiments, the recess 58 may include a trough, such as is shown in presently incorporated U.S. Pat. No. 6,113,637 for allowing translational movement between the respective plates 22, 24.

There are a variety of ways in which the plates 22, 24 can be attached to their corresponding vertebrae 12, 14, including but not limited to using a flange member or keel 60, a lip portion that extends around the vertebral body for receiving one or more bone screws, and other configurations discussed and/or suggested by the presently incorporated references.

Referring to the embodiments of FIGS. 3a-4, both of the plates 22, 24 include a plurality of recesses 62, 64 for receiving one or more elastic members 66 connected by a cord 68. It is understood that the elastic members 66 and/or the cord 68 may be comprised of many different materials, including but not limited to a rubber polymer, resilient metal, or plastic. A coating, such as an ultra-high molecular weight polyethylene (UHMWP), can also be added to an outer surface of the elastic members 66 and/or the cord 68. Furthermore, some or all of the elastic members 66 and/or the cord 68 can be constructed of a bio-resorbable material so that their properties may change over time. Alternatively or in addition, some or all of the elastic members 66 and/or the cord 68 can be constructed of a material that changes properties in response to its environment, such as memory-shape metal. In yet another embodiment, some or all of the elastic members 66 and/or the cord 68 can be made of a material that changes properties in response to an external stimulus, such as a radio-frequency signal. For example, the device 20 may require additional cushioning or constraint during a period in which a spondylolisthesis condition is first addressed, but as the spondylolisthesis resides, the cushioning or constraint can be reduced or removed. In addition, the cord 68 can be used to facilitate the assembly and placement of the members 66 inside the device 20, as well as maintaining the placement during insertion. It is understood that in other embodiments, the cord 68 may not be used. Also, as shown in presently incorporated U.S. Patent Publication No. 2002/0035400 but not shown in the present figures, a sheath can be used to enclose some or all of the area between the two plates 22, 24, including the resilient members 66.

In some embodiments, the shapes of the recesses 62, 64 matingly correspond with the shapes of the elastic members 66. In this way, the elastic members 66 are in continual contact with the plates 22, 24 and thereby provide a constrained cushion therebetween. The amount of cushioning that is provided can be controlled by factors such as the size of each member 66, whether one or more members includes a hollow portion, or the material composition of the members. Also, one or more of the hollow portions of the members can be filled with a material, such as a gel, that affects flexibility. In yet another embodiment, one or more of the hollow portions can be filled with a material that changes over time or in response to other conditions, such as those materials discussed above. Further design choices may also allow some movement other than cushioning, such as movement about one or more of the axis R, L, and T, discussed above.

Referring to the embodiments of FIGS. 5-6, both of the plates 22, 24 include a plurality of recesses 72, 74 for receiving the one or more elastic members 66. In these embodiments, the shapes of one or more of the recesses 72, 74 include one or more gaps 76 when mated with the corresponding elastic members 66. In this way, the elastic members 66 are in continual contact with the plates 22, 24 but are only semi-constrained. This allows some rotational "slide" before the shape of the recesses 72, 74 contact the elastic members 66 in a way to prevent further sliding. It is understood that additional movement may still be provided due to the elastic nature of the members 66. In some embodiments, the gaps 76 may also support an elastic compression and expansion of the members 66 when under a load.

Referring to the embodiments of FIGS. 7-8, the plate 24 includes a plurality of recesses, which may be similar to the recesses 64 (FIG. 4) or 74 (FIG. 6). For the sake of example, the recesses 64 will be further discussed, but it is understood that a broad range of interchangeability between the various features of the different embodiments disclosed herein is intended. The plate 22 includes a recess 82 in the form of a track corresponding with the recesses 64, both for receiving the one or more elastic members 66. In these embodiments, the elastic members 66 are constrained by the recesses 64, yet are allowed to move in the track 82. This allows some sliding inside the track 82, thereby supporting relatively unrestrained radial movement about the axis R. Furthermore, it is understood that additional movement in other directions may still be provided due to the elastic nature of the members 66 or to a wider track 82. In some embodiments, the track 82 may be divided into sections that prevent radial movement pass a predetermined amount.

Referring now to FIG. 9, both of the plates 22, 24 include a plurality of recesses 92, 94 for receiving one or more elastic members 96 connected by a cord 98. The elastic members 96 can have a variety of shapes and/or constructions, with some embodiments having different shapes or constructions in the same device 20. In the present embodiment, the elastic members 96 are shaped as wheels and the shapes of the recesses 92, 94 matingly correspond with the shapes of the elastic members 96. In this way, the elastic members 96 are in continual contact with the plates 22, 24 and thereby provide a constrained cushion therebetween. The amount of cushioning that is provided can be controlled by factors such as the size of each member 96, whether one or more members includes a hollow portion, or the material composition of the members.

The present embodiment provides some unique features. For one, as a rotational motion between the two plates 22, 24 occurs about the axis R, the elastic members 96 will be urged to rotate about an axle 99. The axle 99 may be fixed to one or both of the members 96 and the cord 98, or may allow complete rotation. When the elastic members 96 begin to rotate, this causes a separation to occur between the two plates 22, 24. Another unique feature is that the placement of the cord 98 between the elastic members 96 and the projection 56 helps to keep the device 20 in proper arrangement while it is being inserted in place (in the disc space for the present embodiments). Also, the cord 98 can be used to prevent excessive translational movement, such as when the concave recess 58 includes a trough for promoting such movement.

Referring now to FIGS. 10-11, in other embodiments, the plates 22, 24 include cylindrical shaped recesses 102, 104, respectively. The elastic members 106 are shaped as cylinders and the shapes of the recesses 102, 104 matingly correspond with the shapes of the elastic members. In this way, the elastic members 96 are in continual contact with the plates 22, 24 and thereby provide a cushion therebetween. Depending on the shape and composition of the cylindrical members 106, they can provide a desired amount of constraint in motion in various directions.

Referring to FIGS. 12-17, in other embodiments, the plate 22 includes a recess 112 in the form of a through-hole. The through-hole 112 includes a tapered edge or lip 112a as will be discussed in greater detail below. The plate 24 includes a recess 114 that does not extend all the way through the plate. Elastic members 116 are shaped as cylinders and the shapes of the recesses 112, 114 matingly correspond with the shapes of the elastic members. The elastic members 116 may also include a lip 116a that is shaped to engage with the corresponding lip 112a in the through-hole. In this way, each elastic member 116 can be inserted or dropped through the corresponding through hole 112 and the lips 112a, 116a will "catch" and prevent the elastic member from falling through. Once in place, a locking element 118, such as a screw, a rivet, a rotatable member, or pin, is secured in the through hole. For example, if the locking element 118 is a screw, the through-hole can have a surface for receiving the screw, such as corresponding threads. As a result, the elastic members are secured to the plate 22.

Referring specifically to FIG. 12, in some embodiments, the elastic members 116 are in continual contact with the plate 24 where an end 116b interfaces with the corresponding recess 114. In this embodiment, the elastic members 116 provide a restrained cushion between the plates 22, 24. In some of these embodiments, the lips 116a, 112a do not need to be in contact when the device is fully assembled. Instead, an effective height of each elastic member can be selected by controlling the locking element 118. For example, if the locking element 118 is a screw, the screw can be screwed into the through hole recess 112 a predetermined amount, thereby controlling the amount of the corresponding locking element that extends into the space between the two plates 22, 24. As a result, the plates can be put in various arrangements, including both parallel and non-parallel arrangements, to accommodate the need of the patient.

Referring specifically to FIG. 14, in other embodiments, the elastic members 116 are of a length that they do not "normally" reach their corresponding recess. In some embodiments, such as is illustrated in FIG. 14, there may not even be a corresponding recess in the plate 24 (as compared to the recesses 114 of FIG. 12). In these embodiments, the plates 22, 24 are unrestrained in a "normal" position. A normal position can be one in which the plates 22, 24 are a desired position, such as substantially parallel. A normal position can be out of parallel to allow for the offset nature of the lordotic vertebrae. The position is no longer "normal" when there is substantial movement or flexation of the spine. The elastic members 116 do not affect any rotational movement about the axis R, but provide bumpers between the plates 22, 24 for other movement.

Referring specifically to FIG. 15, in other embodiments, the elastic members 116 can also be of different sizes or shapes to provide different cushioning effects. For example, a relatively long elastic member 116c can be used with a relatively short elastic member 116d. This example can be used in cases of deformity, or can be used to define a relatively normal angulation in the spine. Although a cushioning arrangement is shown, bumper type arrangements can also benefit from these different sized elastic members 116c, 116d.

Referring to FIGS. 16-18, in other embodiments, the elastic members 116 can have a bulbous portion 116e and a neck portion 116g. In addition, one or more of the through-hole recesses 112 can include an insertion opening 112b. During assembly, the neck portion 116g of the elastic members 116 can be slid through the insertion opening 112b until the lip 116a engages with the lip 112a. If the insertion opening 112b is smaller than the through-hole recess 112, then the elastic member 116 can "snap into" the recess and still be sufficiently secured in place.

Referring specifically to FIG. 17, in some embodiments, one or more of the elastic members 116 may include a hollow portion 116f, similar to the hollow portion discussed above with respect to FIGS. 3a-4. This hollow portion 116f provides extra elasticity to the members 116. It is understood that different elastic members 116 can have different sized hollow portions 116f, if at all, to accommodate specific needs for the device 20.

Figure 19:
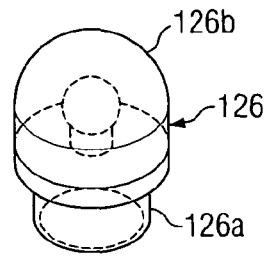

Referring now to FIGS. 18-19, in other embodiments, the plates 22, 24 include a threaded recess 122 and a recess 124, respectively. Pin-shaped elastic members 126 are shaped as cylinders and the shapes of the recesses 122, 124 matingly correspond with the shapes of the elastic members. The elastic members 126 include a threaded end 126a that is shaped to screw into the corresponding threaded recess 122. Once in place, the elastic members 126 are secured to the plate 22. Referring specifically to FIG. 19, in some embodiments, one or more of the elastic members 126 include a hollow portion 126b. Also, it is understood that the threaded end 126a may be in the form of a self-tapping screw and the recess 122 includes a threadable surface such as one made of polyether ether ketone (PEEK).

Figure 21:
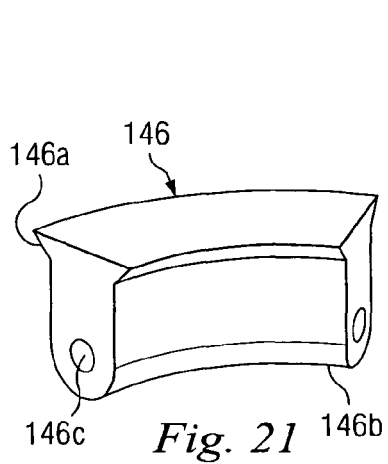
Figure 20:
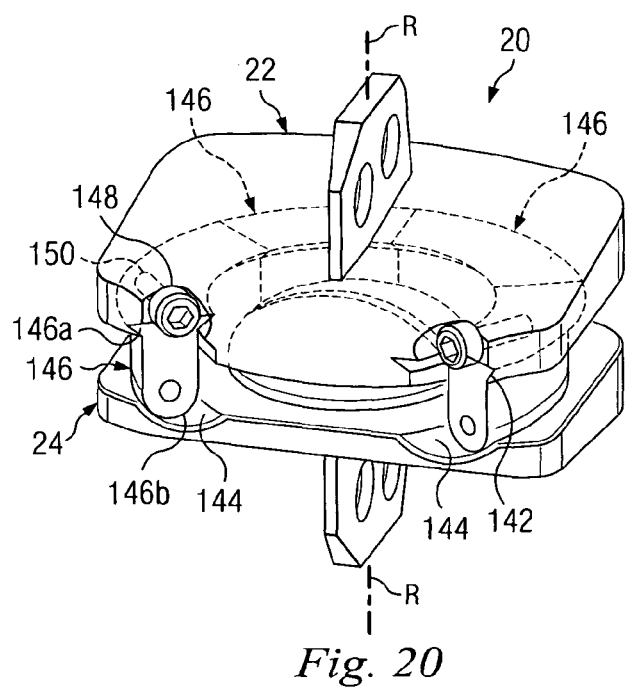
Figure 22:
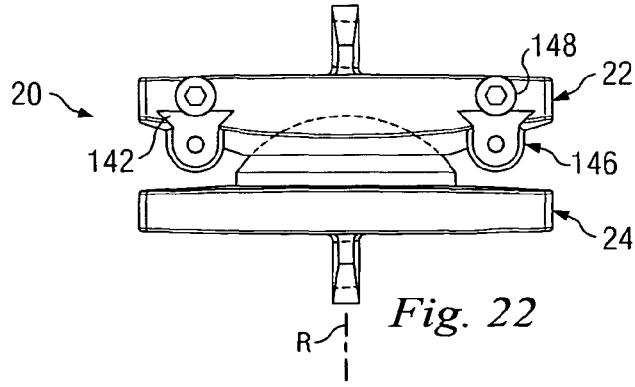

Referring now to FIGS. 20-22, in other embodiments, the plates 22, 24 include a dove-tail recess 142 and a trough recess 144, respectively. Referring specifically to FIGS. 20-21, three elastic members 146 are shaped as quarter-circle arcs with a top portion 146a shaped as a dove-tail for engaging with the dove-tail recess 142, and a bottom portion 146c for sliding in the trough recess 144. Once in place, the elastic members 146 are secured to the plate 22. For some embodiments, additional securement can be obtained by a locking element 148, such as a screw, pin, epoxy, glue, or wedge, inserted into an opening 150. Also in some embodiments, one or more of the elastic members 146 can include an opening 146c which can increase its flexibility and/or compressibility. Referring specifically to FIG. 20, once in place, the elastic members 146 provide compression constraint between the two plates 22, 24, but still allow for rotation about the axis R. Referring specifically to FIG. 22, in other embodiments, the elastic members 146 can provide a spaced bumper between the two plates 22, 24, while still allowing for rotation about the axis R. In these embodiments, the trough recess 144 may not be used, if so desired. Also, the elastic members 146 can be relatively straight and parallel to each other. In this way, the elastic members 146 can be removed from either an anterior or a posterior approach. In some embodiments, there may be locking element s 148 on either or both the anterior and posterior sides of the device 20 to facilitate the subsequent access to the locking elements and hence the elastic members.

Referring now to FIGS. 23-26, in other embodiments, the plates 22, 24 include circular trough recesses 152, 154, respectively. In the present drawing, a single, circular elastic member 156 is positioned between the two trough recesses. For some embodiments, such as is shown in FIGS. 25-26, additional securement can be obtained by locking a portion 158 of the elastic member 156 (in the present embodiment, the portion is connected to the elastic member) with a locking element 160, such as a screw, pin, epoxy, glue, or wedge, inserted into an opening 161. Also in some embodiments, one or more of the elastic members 156 can include a cutaway 156a or an opening 156b which can increase its flexibility and/or compressibility. Once in place, the elastic member 156 provides compression constraint between the two plates 22, 24, but still allows for rotation about the axis R.

Referring now to FIGS. 27-31, in other embodiments, the motion-controlling member 28 can reduce or modify the amount of movement in one or more different directions. Referring specifically to FIGS. 27-28, plates 22, 24 include circular cylindrical recesses 162, 164, respectively. One or more circular elastic members 166 are positioned between the two circular cylindrical recesses 162, 164. The elastic members 166 include ribs 166a, 166b for securing inside the circular cylindrical recesses 162, 164, respectively and may also include openings 166c for varying the amount of flexibility in each elastic member.

Figure 29:
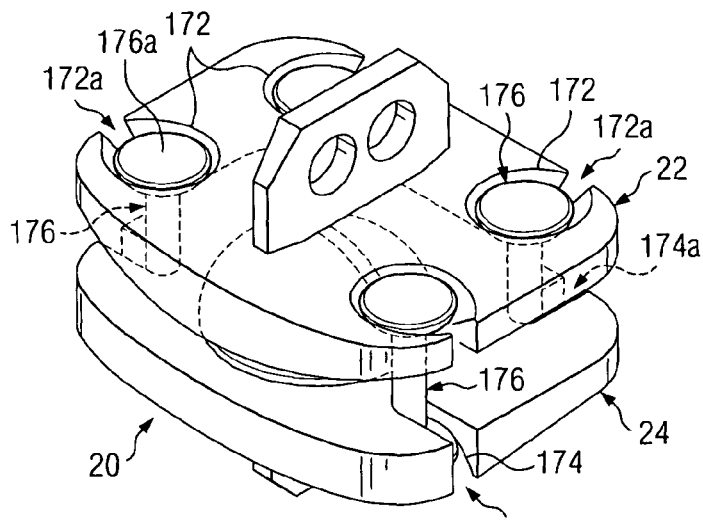
Figure 30:
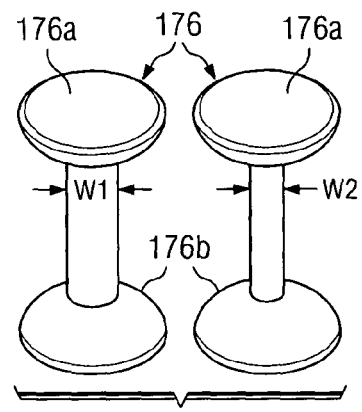
Figure 31:
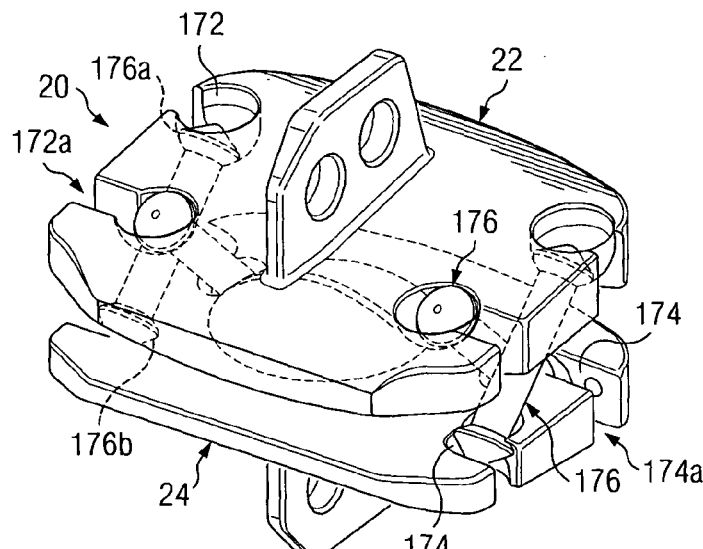
Figure 32:
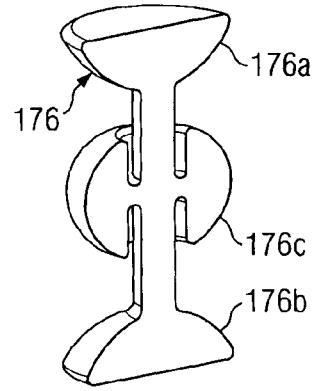

Referring specifically to FIGS. 29-32, plates 22, 24 include through-hole recesses 172, 174, respectively, which can be similar to those discussed above with respect to FIG. 16. Although not required, one or more of the through-hole recesses 172, 174 may include openings 172a, 174a, respectively, for facilitating assembly of the device 20. One or more cylindrical elastic members 176 are positioned between the recesses 172, 174. The elastic members 176 include lips 176a, 176b for securing inside the through-hole recesses 172, 174, respectively and may also include be of varying sizes and/or composition (as shown in FIG. 30) for varying the amount of flexibility in each elastic member. Also, the shape of the elastic members 176 can be modified to achieve various flexibility, cushioning, dampening, or other features. For example, the elastic member 176 in FIG. 32 includes a portion 176c to act as a bumper or cushion.

Figure 33:
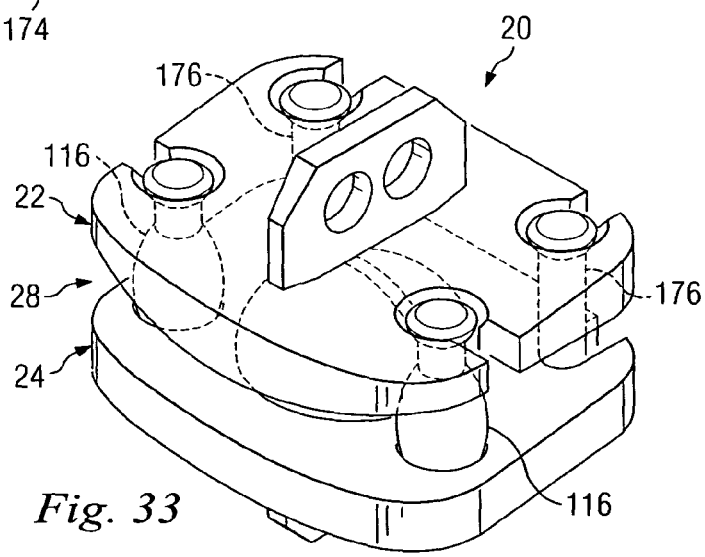

Referring now to FIG. 33, in some embodiments, a wide assortment of different elastic members can be used. In the illustrated examples, two elastic members 176 from FIG. 29 are used in conjunction with two elastic members 116 from FIG. 17. Also, the spacing of the elastic members 116, 117 can be chosen to accommodate a desired effect.

Figure 34:
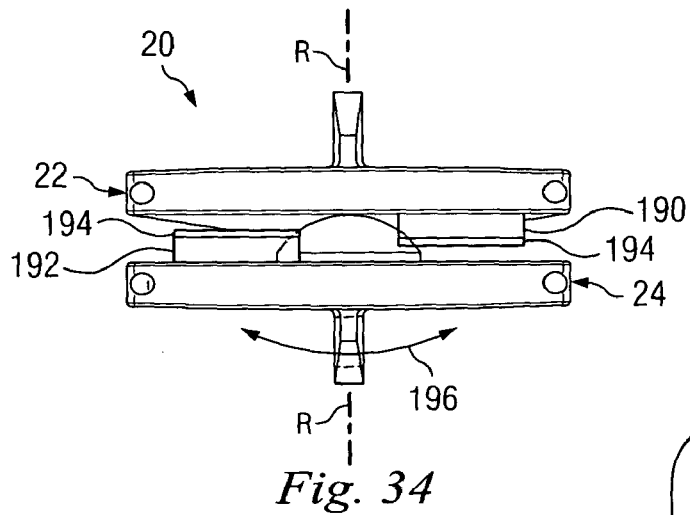
Figure 35:
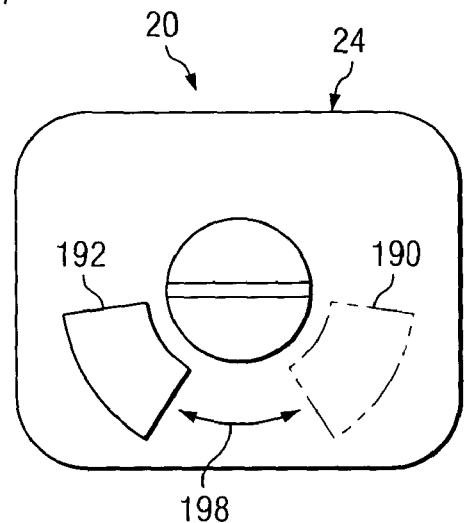
Figure 36:
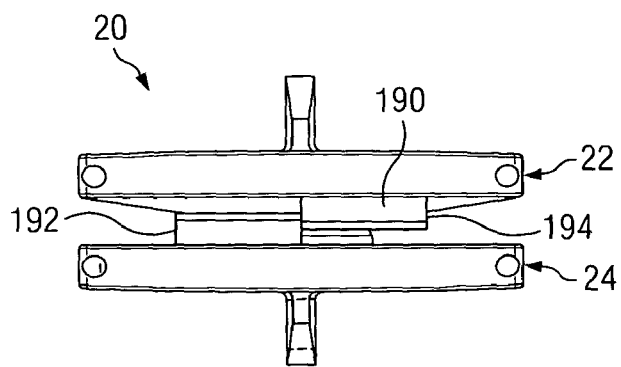

Referring now to FIGS. 34-36, in other embodiments, some elastic members 190 can be attached to one of the plates, e.g., plate 22, and other elastic members 192 can be connected to the opposite plate, e.g., plate 24. Further in these embodiments, the elastic members 190, 192 include a top coating 194, such as UHMWPE, to provide better wear resistance. Partial constraint is provided in the tilting direction shown by reference arrow 196 and rotational direction shown by the reference arrow 198. However, as shown in FIG. 36, when a predetermined amount of rotation occurs, the bumpers 190, 192 "bump," thereby reducing or preventing further rotation 198.

Figure 37:
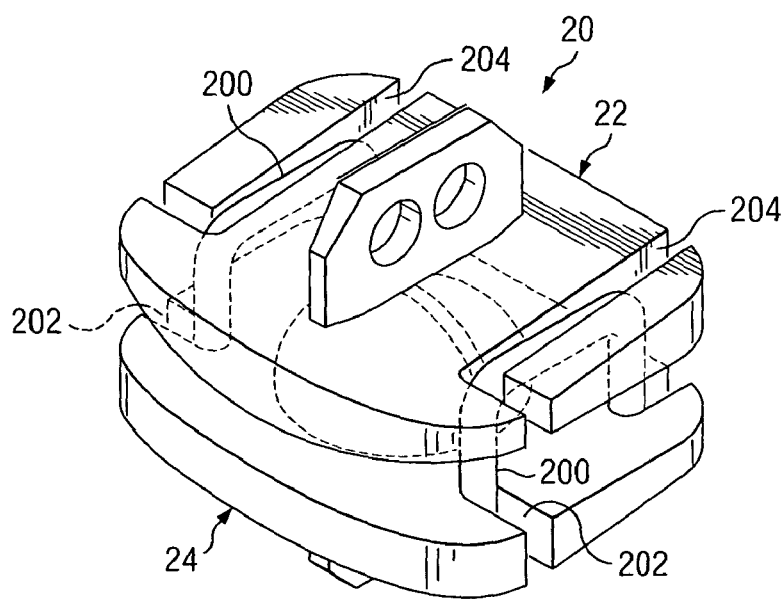
Figure 38:
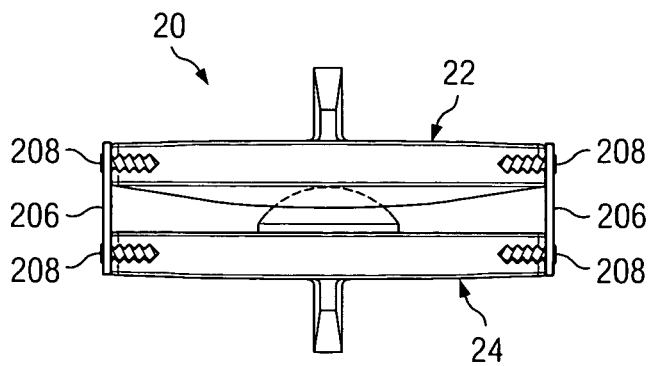
Figure 39:
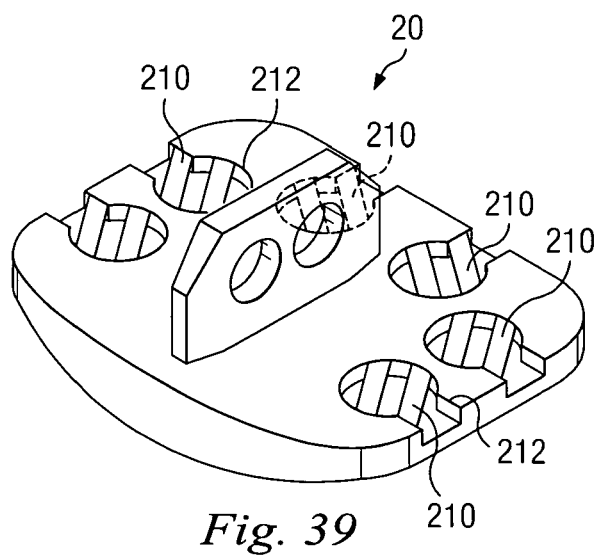

Referring now to FIGS. 37-39, in other embodiments, the elastic members may be positioned on the outer edges of the plates 22, 24. In the embodiment of FIG. 37, one or more elastic members (e.g., stretchable rubber bands) 200 are fitted in slots 202, 204 of the respective plates 22, 24. In the embodiment of FIG. 38, one or more elastic members 206 are attached to the plates 22, 24 via attachment mechanisms 208 such as pins. In the embodiment of FIG. 39, one or more elastic members 210 are fitted into slots 212 of the plate 22 and corresponding slots of the opposing plate 24 (not shown).

Figure 40:
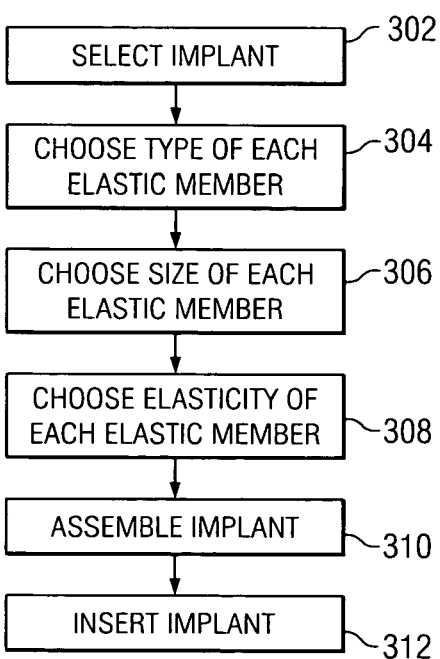
FIG. 40 is a flow chart of a method for inserting a motion-preserving implant according to one embodiment of the present invention.

Referring now to FIG. 40, a method 300 is also provided for implanting the motion-preserving device 20 according to one or more embodiments of the present invention. Although the method 300 applies to procedures outside of the spine, such as the knee or hip, the present examples of a spinal implant will be continued for the sake of simplicity and clarity.

The method 300 begins at step 302 where a particular implant device is selected. At step 304, an elastic member is chosen. As discussed above, there are a wide assortment of elastic members for performing cushioning, dampening, and/or constraint. At step 306, a size of each elastic member is chosen. In some of the above-described examples, deformities such as scoliosis or spondylolisthesis can present patient-specific shapes for the implant device. Also, general curvature of the spine presents different shaped openings, depending on the disc location being addressed.

At step 308, once the elastic member is chosen, the characteristics of the elastic member must be chosen. As described above, it may be desirable for one or more elastic members to have a different range of flexibility than the others. Also, some elastic members may be required to change over time or in response to other conditions. In some embodiments, the characteristics of the elastic member can be modified during the operation, such as by a doctor cutting or notching a portion of the elastic member with a knife.

At step 310, the implant device is assembled with the chosen elastic members, and at step 312, the implant device is inserted into the patient.

The present disclosure has been described relative to several preferred embodiments. Improvements or modifications that become apparent to persons of ordinary skill in the art after reading this disclosure are deemed within the spirit and scope of the application. Accordingly, it is understood that several modifications, changes and substitutions are intended in the foregoing disclosure and, in some instances, some features of the disclosure will be employed without a corresponding use of other features. It is also understood that all spatial references, such as "longitudinal" and "transverse," are for illustrative purposes only and can be varied within the scope of the disclosure. Accordingly, it is appropriate that the appended claims be construed broadly and in a manner consistent with the scope of the disclosure.

The present disclosure includes, but is not limited to, the following numbered items:

1. A motion-preserving implant device comprising: a first plate for engaging with a first bone; a second plate for engaging with a second bone; an articulation member positioned between the two plates; and a motion-controlling member attached to one or both of the plates.

2. The device of item number 1 wherein the motion-controlling member is configured to constrain the relative motion between the two plates.

3. The device of item number 1 wherein the motion-controlling member is configured to dampen the relative motion between the two plates.

4. The device of item number 1 wherein the motion-controlling member is configured to provide a bumper between the two plates when a motion of the two plates meets a predetermined threshold.

5. The device of item number 1 wherein the motion-controlling member includes a plurality of elastic members.

6. The device of item number 5 wherein at least two of the plurality of elastic members are of different shapes.

7. The device of item number 5 wherein at least two of the plurality of elastic members are of different flexibility.

8. The device of item number 5 wherein the plurality of elastic members are configured to position the two plates in a non-parallel configuration.

9. A spinal implant for insertion between two vertebral bodies, comprising: a first plate for engaging with the first vertebral body a second plate for engaging with the second vertebral body an articulation member positioned between the two plates; and an elastic motion-controlling member attached to one or both of the plates.

10. The spinal implant of item number 9 wherein the articulation member and the motion-controlling member are configured to provide pivotal and rotational movement between the two vertebral bodies.

11. The spinal implant of item number 9 wherein the articulation member is configured to provide rotational and translational movement between the two vertebral bodies.

12. The spinal implant of item number 9 wherein the articulation member is a non-elastic ball and socket.

13. The spinal implant of item number 9 wherein the plates are coated with an amorphous oxide coating.

14. The spinal implant of item number 9 wherein the articulation member includes a projection having a convex shape.

15. The spinal implant of item number 9 wherein motion-controlling member includes a coating of an ultra-high molecular weight polyethylene (UHMWP).

16. The spinal implant of item number 9 wherein the motion-controlling member includes a plurality of elastic components.

17. The spinal implant of item number 16 wherein the motion-controlling member includes a cord connected between the plurality of elastic components.

18. The spinal implant of item number 16 wherein at least one of the elastic members is constructed of a bio-resorbable material.

19. The spinal implant of item number 16 wherein at least one of the elastic members is constructed of a material that changes properties in response to its environment.

20. The spinal implant of item number 16 wherein at least one of the elastic members is constructed of a material that changes properties in response to an external stimulus.

21. The spinal implant of item number 16 wherein at least one of the elastic members includes a hollow portion.

22. The spinal implant of item number 16 wherein at least one of the elastic members is filled with a gel.

23. The spinal implant of item number 16 wherein at least one of the elastic members is shaped as a wheel.

24. The spinal implant of item number 16 wherein at least one of the elastic members is shaped as a cylindrical.

25. The spinal implant of item number 16 wherein at least one of the elastic members is shaped as a sphere.

26. The spinal implant of item number 16 wherein at least two of the elastic members are of a different height.

27. The spinal implant of item number 16 wherein at least two of the elastic members are of a different shape.

28. The spinal implant of item number 16 wherein at least two of the elastic members are of a different flexibility.

29. The spinal implant of item number 16 wherein the plates are unrestrained in a first position and are at least partially restrained in a second position by the motion-controlling member.

30. The spinal implant of item number 16 wherein at least one plate includes a plurality of recesses in which one or more of the plurality of elastic members can be inserted.

31. The spinal implant of item number 30 wherein at least one of the elastic members can be snapped into at least one of the recess.

32. The spinal implant of item number 30 wherein at least one of the elastic members can be screwed into at least one of the recess.

33. The spinal implant of item number 30 wherein the plurality of recesses are shaped in a circular dove-tail arrangement.

34. The spinal implant of item number 16 wherein each plate includes at least one recess in which at least one of the plurality of elastic members can be attached and wherein a first of the elastic members can be attached to one of the plates, and a second of the elastic members can be attached to the other of the plates.

35. The spinal implant of item number 16 wherein at least one plate includes at least one recess on a surface that engages with the corresponding vertebral body and receives at least one elastic member.

36. The spinal implant of item number 16 wherein at least one of the elastic members is attached to a plates via an attachment mechanism.

37. The spinal implant of item number 9 wherein at least one of the plates includes a recess that matingly corresponds with the motion-controlling member.

38. The spinal implant of item number 9 wherein at least one of the plates includes a recess for receiving the motion-controlling member.

39. The spinal implant of item number 38 wherein a shape of the recess provides a gap in which the motion-controlling member can slide.

40. The spinal implant of item number 38 wherein the recess is in the form of a track.

41. The spinal implant of item number 38 wherein the recess includes a through-hole through which the motion-controlling member can be inserted.

42. The spinal implant of item number 41 wherein through-hole includes a lip for receiving and engaging with a corresponding lip on the motion-controlling member.

43. The spinal implant of item number 41 further comprising: a locking element for engaging with the through-hole and securing the motion-controlling member therein.

44. The spinal implant of item number 43 wherein the locking element is a screw.

45. A method for inserting a motion-preserving implant between two bones, comprising: determining a desired shape of the motion-preserving implant determining a degree of movement for the motion-preserving implant selecting one or more elastic members according to the determinations of shape and degree of movement assembling the one or more elastic members into the motion-preserving implant; and inserting the assembled motion-preserving implant device between the two bones.

46. The method of item number 45 further comprising: selecting the motion-preserving implant from a plurality of differently configured implants after determining either the desired shape, the degree of movement, or both.

47. A kit for use in a surgery addressing a joint between two bones, comprising: at least one motion-preserving implant, the motion-preserving implant having at least one recess for receiving at least one elastic member; and a plurality of elastic members for use with the motion-preserving implant, the plurality of elastic members for providing a plurality of different configurations of a motion-preserving implant when received therein.

48. The kit of item number 47 wherein the motion-preserving implant is configured to accept a plurality of different shaped elastic members.

49. The kit of item number 47 wherein the motion-preserving implant is configured to accept a plurality of different shaped elastic members.

50. The kit of item number 47 wherein the elastic members are similarly shaped, but provide different levels of flexibility.

What is claimed is:

1. A motion-preserving implant device comprising:
   a first plate comprising an outer surface for engaging with a first bone and an inner surface including both a plurality of first discrete recessed surfaces and a concave articulation surface, the plurality of first recessed surfaces spaced outwardly apart from the concave articulation surface in a circumscribing relationship therewith;
   a second plate for engaging with a second bone, the second plate comprising a plurality of second discrete recessed surfaces;
   a convex articulation member positioned entirely between the two plates and in direct and slidable contact with the concave articulation surface;
   a plurality of separate and spaced motion-controlling members each extending between an opposing pair of the first and second recessed surfaces, wherein the articulation member is separate from and stiffer than the motion-controlling members; and
   an elongated member connected to and joining the plurality of motion-controlling members, the elongated member extending between adjacent motion controlling members in a manner that maintains the spacing of the spaced motion controlling members.

2. The device of claim 1 wherein the motion-controlling members are configured to constrain the relative motion between the two plates.

3. The device of claim 1 wherein the motion-controlling members are formed from an elastic material.

4. The device of claim 1 wherein:
   the elongated member is of a flexible material.

5. The device of claim 1 wherein:
   the elongated member extends through the plurality of motion-controlling members.

6. A spinal implant for insertion between two vertebral bodies, comprising:
   a first plate comprising an outer surface for engaging with the first vertebral body and an inner surface including both a plurality of first discrete recessed surfaces and a concave articulation surface, the first recessed surfaces adjacent to and outwardly circumscribing the concave articulation surface;

a second plate for engaging with the second vertebral body, the second plate comprising a plurality of second discrete recessed surfaces aligned with and facing the plurality of first recessed surfaces;

an articulation member made from a first material and positioned in direct and articulating engagement with the concave articulation surface and entirely between the two plates;

a plurality of separate and spaced elastic motion-controlling members made from a second material, each motion-controlling member extending between an opposing pair of the first and second recessed surfaces, the second material being more elastic than the first material; and an elongated member connected to and joining the plurality of motion-controlling members, the elongated member extending between adjacent motion controlling members in a manner that maintains the spacing of the spaced motion controlling members.

7. The spinal implant of claim 6 wherein the articulation member and the motion-controlling members are configured to provide pivotal and rotational movement between the two vertebral bodies.

8. The spinal implant of claim 6 wherein the articulation member is configured to provide rotational and translational movement between the two vertebral bodies.

9. The spinal implant of claim 6 wherein the articulation member is a non-elastic ball and socket.

10. The spinal implant of claim 6 wherein the plates are coated with an amorphous oxide coating.

11. The spinal implant of claim 6 wherein the articulation member includes a projection having a convex shape.

12. The spinal implant of claim 6 wherein at least one of the elastic members is constructed of a bio-resorbable material.

13. The spinal implant of claim 6 wherein at least one of the elastic members is constructed of a material that changes properties in response to its environment.

14. The spinal implant of claim 6 wherein at least one of the elastic members is constructed of a material that changes properties in response to an external stimulus.

15. The spinal implant of claim 6 wherein at least one of the elastic members includes a hollow portion.

16. The spinal implant of claim 6 wherein at least one of the elastic members is filled with a gel.

17. The spinal implant of claim 6 wherein at least one of the elastic members is shaped as a wheel.

18. The spinal implant of claim 6 wherein at least one of the elastic members is shaped as a sphere.

19. The spinal implant of claim 6 wherein:
the elongated member is of a flexible material.

20. The spinal implant of claim 6 wherein:
the elongated member extends through the plurality of motion-controlling members.

21. An implant comprising:
a first plate for engaging with a first bone comprising a superior surface and an inferior surface, the superior surface having both a plurality of discrete recessed surface portions and a convex articulation surface portion, the recessed surface portions adjacent to and outwardly circumscribing the convex articulation surface portion;
a second plate for engaging with a second bone comprising a superior surface and an inferior surface, the inferior surface having a concave articulation surface portion in direct contact and articulating engagement with the convex articulation surface portion;
a plurality of separate and spaced motion-controlling members, separate from the convex articulation surface portion, extending between the recessed surface portions and the inferior surface of the second plate; and
an elongated member connected to and joining the motion-controlling members, the elongated member extending between adjacent motion controlling members in a manner that maintains the spacing of the spaced motion controlling members.

22. The implant of claim 21 wherein;
the elongated member is of a flexible material.

23. The implant of claim 21 wherein:
the elongated member extends through the plurality of motion-controlling members.

24. A motion-preserving implant device comprising:
a first plate member having a plurality of discrete recessed surfaces;
a second plate member disposed in a spaced apart, facing and generally parallel relationship with the first plate member;
an articulation member centrally disposed between the first and second plate members; and
a plurality of separate and spaced motion controlling members disposed between the first and second plate members, outwardly circumscribing the articulation member, and being strung together, necklace-like, by an elongated joining member, the articulation member being stiffer than the motion controlling members, the elongated joining member extending between adjacent motion controlling members in a mariner that maintains the spacing of the spaced motion controlling members.

25. A motion-preserving implant device comprising:
a first plate comprising an outer surface for engaging with a first bone and an inner surface including both a plurality of first recessed surfaces and a concave articulation surface, the plurality of first recessed surfaces spaced outwardly apart from the concave articulation surface in a circumscribing relationship therewith;
a second plate for engaging with a second bone, the second plate comprising a plurality of second recessed surfaces;
a convex articulation member positioned entirely between the two plates and in direct and slidable contact with the concave articulation surface;
a plurality of motion-controlling members each extending between an opposing pair of the first and second recessed surfaces, the motion-controlling members being distributed substantially on three sides of the convex articulation member, a fourth side being devoid of motion-controlling members such that the motion controlling members are non-symmetrically distributed about the convex articulation member; and
an elongated member connected to and joining the plurality of motion-controlling members.

26. The motion-preserving implant device of claim 25, wherein the elongated member and the motion controlling members form a complete ring about the convex articulation member.

* * * * *